United States Patent
Tsai et al.

(10) Patent No.: US 9,376,412 B2
(45) Date of Patent: Jun. 28, 2016

(54) ANODE MATERIAL WITH UNSATURATED COMPOUNDS BONDED TO CARBON-CONTAINING SUBSTRATES AND ANODE ELETRODE PLATE

(75) Inventors: Li-Duan Tsai, Hsinchu (TW); Wei-Hsin Wu, Kaohsiung (TW); Yueh-Wei Lin, Hsinchu County (TW); Chia-Chen Fang, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 1051 days.

(21) Appl. No.: 13/452,949

(22) Filed: Apr. 23, 2012

(65) Prior Publication Data

US 2013/0171515 A1 Jul. 4, 2013

(30) Foreign Application Priority Data

Dec. 30, 2011 (TW) .............................. 100149704 A

(51) Int. Cl.
*H01M 4/02* (2006.01)
*C07D 307/42* (2006.01)
*B82Y 30/00* (2011.01)
*H01M 4/133* (2010.01)
*H01M 4/36* (2006.01)
*H01M 4/587* (2010.01)
(Continued)

(52) U.S. Cl.
CPC .............. *C07D 307/42* (2013.01); *B82Y 30/00* (2013.01); *C07D 207/448* (2013.01); *C07D 207/452* (2013.01); *H01M 4/133* (2013.01); *H01M 4/366* (2013.01); *H01M 4/587* (2013.01); *H01M 4/62* (2013.01); *H01M 10/4235* (2013.01); *H01M 4/628* (2013.01); *H01M 10/0525* (2013.01); *Y02E 60/122* (2013.01)

(58) Field of Classification Search
CPC ..... H01M 4/133; H01M 4/1393; H01M 4/60; H01M 4/366; H01M 4/587; H01M 10/4235; H01M 4/62; H01M 4/628; H01M 10/0525; B82Y 30/00; C07D 307/42; C07D 207/452; C07D 207/448; Y02E 60/122
USPC ................................................ 429/211, 231.8
See application file for complete search history.

(56) References Cited

U.S. PATENT DOCUMENTS

| 5,756,062 | A | 5/1998 | Greinke et al. | |
| 6,228,942 | B1 * | 5/2001 | Michot et al. | 525/183 |

(Continued)

FOREIGN PATENT DOCUMENTS

| CN | 1848488 | 10/2006 |
| CN | 101023543 | 8/2007 |

(Continued)

OTHER PUBLICATIONS

Cheng, Qunfeng, et al. "Functionalized Carbon Nanotube Sheet/Bismaleimide Nanocomposites: Mechanical and Electrical Performance Beyond Carbon-Fiber Composites." Small 6.6 (2010): 763-767.*

(Continued)

*Primary Examiner* — Gary Harris
(74) *Attorney, Agent, or Firm* — Jianq Chyun IP Office

(57) ABSTRACT

An anode material is provided for a surface of an electrode. The anode material comprises carbon-containing substrates and unsaturated compounds. At least one chemical bond is formed between the unsaturated compounds and the surfaces of the carbon-containing substrates.

11 Claims, 10 Drawing Sheets

(51) Int. Cl.
*H01M 4/62* (2006.01)
*H01M 10/42* (2006.01)
*C07D 207/448* (2006.01)
*C07D 207/452* (2006.01)
*H01M 10/0525* (2010.01)

(56) References Cited

U.S. PATENT DOCUMENTS

| | | | |
|---|---|---|---|
| 7,736,804 B2 | 6/2010 | Kim et al. | |
| 7,754,375 B2 | 7/2010 | Fujikawa et al. | |
| 7,951,489 B2 | 5/2011 | Kim et al. | |
| 2005/0287440 A1 | 12/2005 | Chang et al. | |
| 2006/0134516 A1 | 6/2006 | Im et al. | |
| 2007/0015053 A1 | 1/2007 | Morris | |
| 2008/0160405 A1* | 7/2008 | Yang | H01M 4/131 429/215 |
| 2008/0199773 A1* | 8/2008 | Deguchi et al. | 429/188 |
| 2009/0053606 A1 | 2/2009 | Kim et al. | |
| 2009/0214958 A1 | 8/2009 | Park | |

FOREIGN PATENT DOCUMENTS

| | | |
|---|---|---|
| CN | 101807724 | 8/2010 |
| TW | 200610216 | 3/2006 |
| TW | 200610785 | 4/2006 |
| TW | 201116574 | 5/2011 |

OTHER PUBLICATIONS

"Office Action of Taiwan Counterpart Application", issued on Dec. 18, 2013, p. 1-p. 16, in which the listed references were cited.

Cvelbar et al.,"Formation of functional groups on graphite during oxygen plasma treatment," Applied Surface Science 253, 2006, pp. 1861-1865.

Wang et al, "Electrochemical characteristics of tin-coated MCMB graphite as anode in Lithium-ion cells," Electrochimica Acta 50, 2004, pp. 517-522.

Sarkar et al., "Diels-Alder Chemistry of Graphite and Graphene: Graphene as Diene and Dienophile," J. Am. Chem. Soc. 133, 2011, pp. 3324-3327.

"Office Action of China Counterpart Application", issued on Sep. 3, 2014, p. 1-p. 9, in which the listed references were cited.

* cited by examiner

ANODE MATERIAL WITH UNSATURATED COMPOUNDS BONDED TO CARBON-CONTAINING SUBSTRATES AND ANODE ELETRODE PLATE

CROSS-REFERENCE TO RELATED APPLICATION

This application claims the priority benefit of Taiwan application serial no. 100149704, filed on Dec. 30, 2011. The entirety of the above-mentioned patent application is hereby incorporated by reference herein and made a part of this specification.

BACKGROUND OF THE APPLICATION

1. Field of Application

The present application relates to a surface modifier for an electrode plate of a lithium battery and to the electrode plate of the lithium battery. More particularly, the present application relates to an anode material with self-hilling ability and to an anode electrode plate.

2. Description of Related Art

Since one-time used battery does not full fill the requirement of the environmental protection, the battery system capable of being recharged is getting a lot of interests. With the rapid development and popularization of the portable electronic products, the lithium batteries which can repeat the cycle of discharging-and-recharging have the advantages of light weight, high voltage and high energy density so that the market demands on the lithium batteries increase. Comparing with the lead-acid battery, the nickel-metal-hydride battery, the nickel-zinc battery and the nickel-cadmium battery, the lithium battery has the advantages of high working voltage, large energy density, light weight, long lifetime and good environmental protection and the lithium battery is one of the best batteries for being applied in the flexible battery in the future. Hence, the demands on the properties of the lithium battery, such as light weight, durability, high working voltage, high energy density and safety become high. Further, the developmental potential and the application of the lithium batteries in the light-weighted electromobile industry, electric motor car industry and large-sized electronic storage industry are high.

However, in the current technology, the solvation of the lithium ions in the lithium battery with the solvent occurs and at least one lithium ion can attract multiple solvent molecules to perform the solvation. When the lithium ions attracting the electrolyte molecules to perform the solvation is close to the anode electrode plate, the lithium ions with the solvent molecules easily lead to delamination of the anode electrode while most of the anode electrode plate is the graphitized carbon material having the interlayer structure. Thus, in the current technology, a solid electrolyte interface film (SEI film) is formed on the surface of the anode electrode plate so that the lithium ions depart from the solvation solvent molecules while the lithium ions attracting the electrolyte molecule to occur the solvation in the electrolyte pass through the SEI film and enter the anode electrode plate. Thus, the delamination of the anode electrode plate can be prevented. Currently, there are two types of SEI film include the reaction-type SEI film and the reductive-type SEI film. Nevertheless, those SEI films are added into the electrolyte in a form of additive and the SEI films formed from the additives by performing the electrochemical polymerization adsorb the surface of the anode electrode plate. Hence, the polymerization effect and the ability to detach the solvent molecules of the SEI films are limited by the effect of the electrochemical polymerization of themselves. In addition, the SEI film polymerized on the anode electrode plate is easily dissolved in the electrolyte, which affects the electrical performance. Moreover, the SEI film covers the anode electrode plate by adsorption so that it is easy to detach the SEI film from the anode electrode plate while the anode electrode plate is operated in a high temperature. Thus, the performance of the adsorbability of the SEI film affects the ability of the SEI film to detach the solvent molecules from the lithium ions. Further, it is easy to produce gas during the polymerization is performed to form the SEI film, which affects the whole performance of the SEI film.

SUMMARY

The present application provides an anode material which can be formed as protective layers having self-hilling ability on the carbon-containing substrates and is capable of improving the electrochemical activity of the carbon-containing substrates.

The application provides an anode electrode plate having protective layers which form chemical bonds with surfaces of a carbon-containing substrates and capable of improving the compatibility between the surfaces of the carbon-containing substrates and the electrolyte and preserving the unity of the carbon-containing substrates.

In the present application, an anode material is provided for a surface of an electrode. The anode material comprises carbon-containing substrates and unsaturated compounds. The unsaturated compounds form at least a chemical bond with the surfaces of the carbon-containing substrates.

In the present application, an anode electrode plate is provided. The anode electrode plate comprises a current collector and an anode material. The anode material is disposed on the current collector and the anode material includes carbon-containing substrates and unsaturated compounds. The unsaturated compounds form at least a chemical bond with the surfaces of the carbon-containing substrates.

Accordingly, in the present application, the addition reactions are performed between the functional groups of the unsaturated chemical compounds and the surfaces of the carbon-containing substrates to form chemical bonds such as covalent bonds. Most of the reactions are reversible. When a portion of the crosslinking structures of the polymer of the unsaturated compounds which form chemical bonds with the surfaces of the carbon-containing substrates is damaged by the external factors (such as heat or stress), the damaged crosslinking structures can recover from applying energy (such as heating) onto the polymer to perform the addition reactions again due to the reversibility of the addition reactions. Thus, on the surfaces of the carbon-containing substrates, the protective layers which are made of the unsaturated chemical compounds having chemical bonds with the surfaces of the carbon-containing substrates possess self-hilling ability. Moreover, the protective layers which are formed from the unsaturated chemical compounds on the carbon-containing substrates can improve the electrochemical activity of the surfaces of the carbon-containing substrates, improve the compatibility between the surfaces of the carbon-containing substrates and the electrolyte and, meanwhile, preserve the unity of the original carbon-containing substrates.

It is to be understood that both the foregoing general description and the following detailed description are exemplary, and are intended to provide further explanation of the application as claimed.

BRIEF DESCRIPTION OF THE DRAWINGS

The accompanying drawings are included to provide a further understanding of the application, and are incorporated in and constitute a part of this specification. The drawings illustrate embodiments of the application and, together with the description, serve to explain the principles of the application.

DESCRIPTION OF THE PREFERRED EMBODIMENTS

Figure 1:
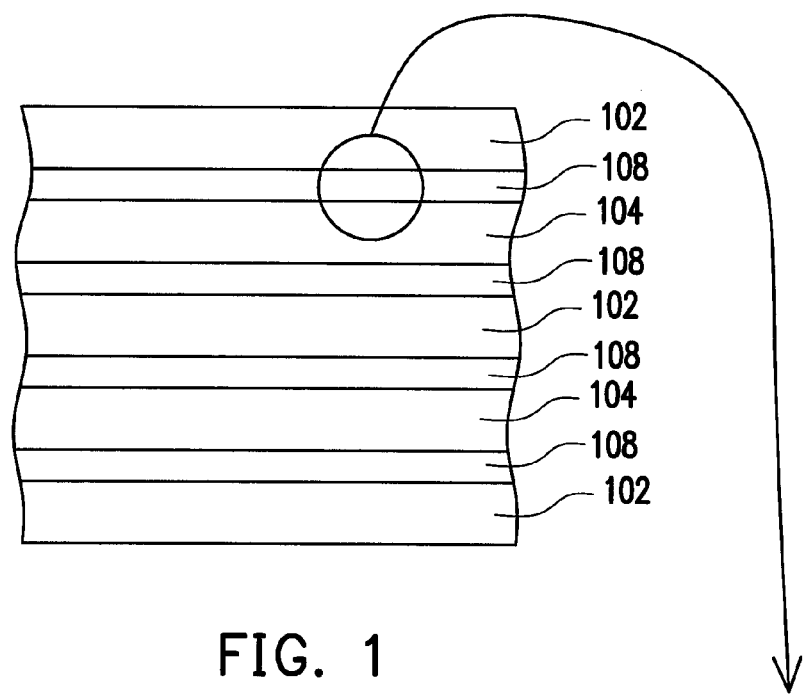
FIG. 1 is a schematic cross-sectional view of a portion of a lithium battery according to one embodiment of the present application.
Figure 1A:
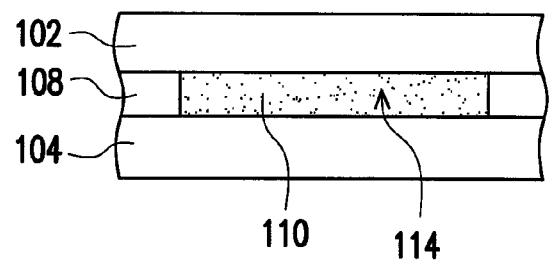
FIG. 1A is a partial enlargement view of the cross-section of the lithium battery shown FIG. 1.

FIG. 1 is a schematic cross-sectional view of a portion of a lithium battery according to one embodiment of the present application. FIG. 1A is a partial enlargement view of the cross-section of the lithium battery shown FIG. 1. As shown in FIG. 1 and FIG. 1A, the lithium battery 100 of the present embodiment comprises several cathode electrode plates 102, several anode electrode plates 104, several layers of separators 108 and an electrolyte 110. The cathode electrode plates 102 and the anode electrode plates 104 are alternatively arranged and are stacked on one another. Further, for a pair of one cathode electrode plate 102 and one anode electrode plate 104, there is one separator 108 disposed between the cathode electrode plate 102 and the anode electrode plate 104. Each of the separators 108 can be formed of, for example but not limited to, a porous structure. That is, the holes of the porous structure uniformly distribute in the whole separator 108. The cathode electrode plates 102, the separators 108 and the anode electrode plates 104 which are stacked on one another are Soaked in the electrolyte 110. That is, the whole body of the battery is flood with the electrolyte 110. On the other words, the spaces between the cathode electrode plates 102, the anode electrode plates 104 and the separators 108 are flooded with the electrolyte 110 and, that is, the holes 114 of the separator 108 are flooded with the electrolyte 110.

The cathode electrode plates 102 can be made of, for example, lithium mixed metal oxide, such as $LiMnO_2$, $LiMn_2O_4$, $LiCoO_2$, $Li_2Cr_2O_7$, $Li_2CrO_4$, $LiNiO_2$, $LiFeO_2$, $LiNi_xCo_{1-x}O_2(0<x<1)$, $LiMPO_4$ (M=transition metal), $LiMn_{0.5}Ni_{0.5}O_2$, $LiNi_xCo_yMn_zO_2(x+y+z=1)$, $LiNi_xCo_yAl_zO_2(x+y+z=1)$, $LiMc_{0.5}Mn_{1.5}O_4$ or the combination thereof, wherein Mc is a metal with valence of two.

The anode electrode plates 104 can be made of, for example, graphite, graphene, hard carbon, soft carbon, single-wall carbon nano-tubes (SWCNT), multi-wall carbon nano-tubes (MWCNT), carbon fiber, carbon alloy, carbon metal oxide, silicon carbon composite (Si/C composite), mesophase carbon micro beads (MCMB), mesophase graphite, mesoporous graphite or the combination thereof.

The separators 108 includes insulating material such as polyethylene (PE), polypropylene (PP), polytetrafluoroethylene (PTFE) film, polyamide film, poly vinyl chloride (PVC) film, polyvinylidine fluoride (PVDF) film, polyaniline (PAN) film, polyimide film, nonwoven fabrics, polyethylene terephthalate, polystyrene (PS), cellulose or the multi-layered complex structure thereof such as PE/PP/PE. The main composition of the electrolyte 110 includes organic solvent, lithium salt and additive. The organic solvent can be, for example, γ-butyrolactone (GBL), ethylene carbonate (EC), propylene carbonate (PC), diethyl carbonate (DEC), propyl acetate (PA), dimethyl carbonate (DMC), ethylmethyl carbonate (EMC) or the combination thereof. The lithium salt can be, for example, $LiPF_6$, $LiBF_4$, $LiAsF_6$, $LiSbF_6$, $LiClO_4$, $LiAlCl_4$, $LiGaCl_4$, $LiNO_3$, $LiC(SO_2CF_3)_3$, $LiN(SO_2CF_3)_2$, $LiSCN$, $LiO_3SCF_2CF_3$, $LiC_6F_5SO_3$, $LiO_2CCF_3$, $LiSO_3F$, $LiB(C_6H_5)_4$, $LiCF_3SO_3$, $LiB(C_2O_4)_2$ or the combination thereof.

Figure 2:
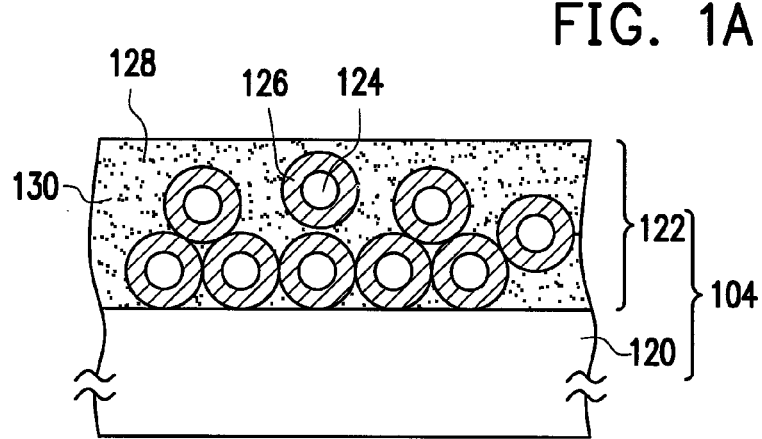
FIG. 2 is a partial enlargement view of a cross-section of an anode electrode plate of a lithium battery according to one embodiment of the present application.

FIG. 2 is a partial enlargement view of a cross-section of an anode electrode plate of a lithium battery according to one embodiment of the present application. As shown in FIG. 1 and FIG. 2, the anode electrode plate 104 of the present embodiment comprises a current collector 120 and an anode material layer 122. The anode material layer 122 is located on the current collector 120 and the anode material layer 122 comprises carbon-containing substrates 124 and protective layers 126 covering the surfaces of the carbon-containing substrates 124. Furthermore, the anode material layer 122 comprises a conducting agent 128 and a binder 130. In one embodiment, the carbon-containing substrates 124 include, for example, mesophase carbon micro beads (MCMB), mesophase graphite, graphite, graphene, hard carbon, soft carbon, single-wall carbon nano-tubes (SWCNT), multi-wall carbon nano-tubes (MWCNT), carbon fiber, carbon alloy, carbon metal oxide, silicon carbon composite (Si/C composite), mesoporous graphite or the combination thereof. The graphitization degree of the carbon-containing substrates 124 is about 40%~100%. For instance, the graphitization degree of the MCMB is about 78% and the graphitization degree of the mesophase graphite is about 67%.

Moreover, the protective layer 126 is a solid electrolyte interface film (SEI film) which is composed of an unsaturated compounds. The unsaturated compounds have at least one chemical bond with the surfaces of the carbon-containing substrates 124. It should be noticed that the chemical bonds can be, for example, the covalent bonds. That is, when the surfaces of the carbon-containing substrates 124 bond with the unsaturated compounds, the graphitization degree of the carbon-containing substrates is slightly decreased and the graphitization degree of the bonded carbon-containing substrates is about 50%~90%. Moreover, the aforementioned unsaturated compounds comprise at least one diene functional group or at least one dienophile functional group to chemically bond with the surfaces of the carbon-containing substrates 124. Further, the aforementioned unsaturated compounds comprise maleimide, furan, thiophene, pyrrole, alkyne, alkene or cycloalkene.

In addition, the aforementioned unsaturated compounds comprise at least a functional segment such as the segment which can aid the transmission of the lithium ions. The functional segment comprises ethylene oxide segment, fluorocarbon segment, siloxane segment, aliphatic segment, aromatic segment or the combination thereof. The weight percentage of the unsaturated compounds to the carbon-containing substrates 124 is smaller than 15 wt % and the thickness of each of the protective layers 126 made of the unsaturated compounds and covering the carbon-containing substrates 124 is about 5~500 nm.

Further, in one embodiment, the aforementioned unsaturated compounds can be, for example, represented by the chemical formula (I) shown as following:

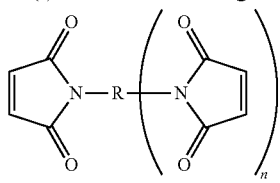

Wherein, R comprises at least one unit of ethylene oxide segment, propylene oxide segment, siloxane segment, aliphatic segment, aromatic segment, fluorocarbon segment or the combination thereof, and n is 1~3.

In another embodiment, the aforementioned unsaturated compounds comprise, for example, the chemical structure (II) shown as following:

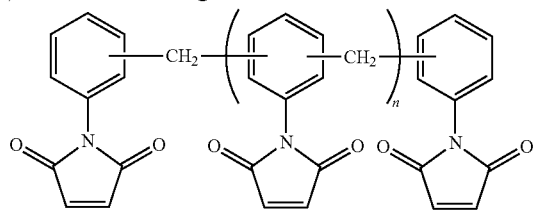

Wherein, n is 0~4.

In the other embodiment, the aforementioned unsaturated compounds comprise, for example, the chemical structure (III) shown as following:

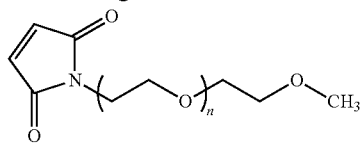

Wherein, n is 1~10.

In one embodiment, the aforementioned unsaturated compounds comprise, for example, the chemical structure (IV) shown as following:

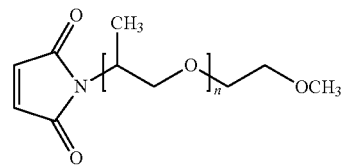

Wherein, n is 1~10.

In one embodiment, the aforementioned unsaturated compounds comprise, for example, the chemical structure (V) shown as following:

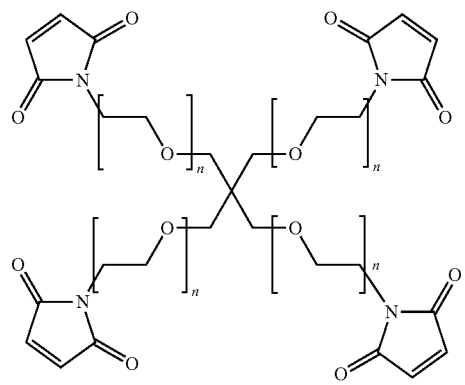

Wherein n is 1~11.

In one embodiment, the aforementioned unsaturated compounds can be represented by, for example, the chemical formula (VI) shown as following:

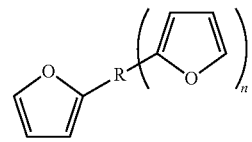

Wherein, R comprises at least one unit of ethylene oxide segment, propylene oxide segment, siloxane segment, aliphatic segment, aromatic segment, fluorocarbon segment or the combination thereof, and n is 0~1.

In one embodiment, the aforementioned unsaturated compounds comprise, for example, the chemical structure (VII) shown as following:

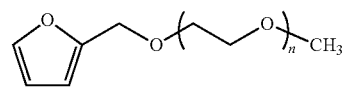

Wherein, n is 0~1.

In one embodiment, the unsaturated compounds having diene functional groups comprise, for example, the chemical structure (VIII) shown as following:

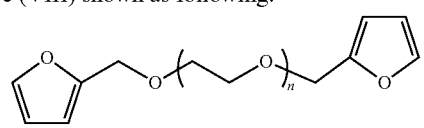

Wherein n is 1~10.

Moreover, in another embodiment, the aforementioned unsaturated compounds can be represented by, for example, the chemical formula (IX) shown as following:

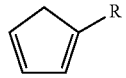

Wherein, R comprises at least one unit of ethylene oxide segment, propylene oxide segment, siloxane segment, aliphatic segment, aromatic segment, fluorocarbon segment or the combination thereof.

In one embodiment, the aforementioned unsaturated compounds comprise, for example, the chemical structure (X) shown as following:

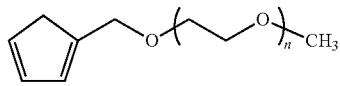

Wherein, n is 1~10.

Furthermore, the aforementioned unsaturated compounds can be represented by, for example, the chemical formula (XI) shown as following:

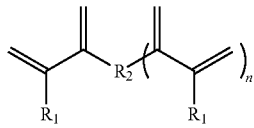

Wherein, R1 comprises hydrogen group, methoxy group, alkyl group or phenyl group. R2 comprises at least one unit of hydrogen, ethylene oxide segment, propylene oxide segment, siloxane segment, aliphatic segment, aromatic segment, fluorocarbon segment or the combination thereof, and n is 0~4.

In one embodiment, the aforementioned unsaturated compounds comprise, for example, the chemical structure (XII) shown as following:

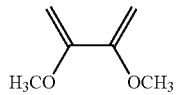

In addition, in the another embodiment, the aforementioned unsaturated compounds can be represented by, for example, the chemical formula (XIII) shown as following:

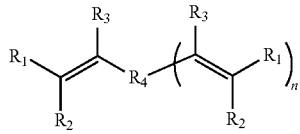

Wherein, R1, R2 and R3 comprise hydrogen, cyano group, carboxyl group, methoxycarbonyl group, halogen or imide group. R4 comprises at least one unit of hydrogen, cyano group, ethylene oxide segment, propylene oxide segment, siloxane segment, aliphatic segment, aromatic segment, fluorocarbon segment or the combination thereof, and n is 0~4.

In one embodiment, the aforementioned unsaturated compounds comprise, for example, the chemical structure (XIV) shown as following:

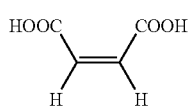

Moreover, in the other embodiment, the aforementioned unsaturated compounds can be represented by, for example, the chemical formula (XV) shown as following:

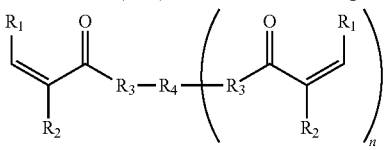

Wherein, R1 comprises hydrogen or carboxylmethylene group, R2 comprises hydroxy group, hydrogen or methyl group, R3 comprises oxygen or amino group, and R4 comprises at least one unit of ethylene oxide segment, propylene oxide segment, siloxane segment, aliphatic segment, aromatic segment, fluorocarbon segment or the combination thereof, and n is 0~4.

In one embodiment, the aforementioned unsaturated compounds comprise, for example, the chemical structure (XVI) shown as following:

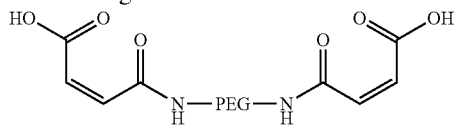

In the following paragraphs, the manufacturing process of the anode electrode plate of the present application is described and several embodiments of the unsaturated compounds having the chemical bonds with the carbon-containing substrates in the anode material layer are illustrated. The NMR data of the unsaturated compounds used in the embodiments illustrated later are listed thereafter. NMR data of Phenylmethane maleimide 2300 (BMI2300) are: $^1$H NMR (200 MHz, DMSO-d$_6$), δ 7.38-7.055 (m, 5.14nH), 4.02 (s, nH). NMR data of N,N'-diphenylmethane bismaleimide 110. (BMI1100) are: $^1$H NMR (200 MHz, DMSO-d$_6$), δ 7.35 (d, J=7.8 Hz, 4H), 7.25 (d, J=7.8 Hz, 4H), 7.15 (s, 4H), 4.02 (s, 2H). NMR data of N-(2-(2-ethoxyethoxy)ethyl)-maleimide (MImEO) are: $^1$H NMR (200 MHz, CDCl$_3$), δ 6.68 (s, 2H), 3.72-3.45 (m, 8H), 1.16 (t, J=8 Hz, 3H). NMR data of N-(methoxy-polyethylene glycol 550)-maleimide (MImPEO) are: $^1$H NMR (200 MHz, CDCl$_3$), δ 6.67 (s, 2H), 3.68-3.49 (m, 44H), 3.34 (s, 3H). NMR data of N,N'-(Jeffamine® D400) bismaleimide (BMID400) are: $^1$H NMR (200 MHz, CDCl$_3$), δ 6.68 (s, 2H), 3.72-3.45 (m, 8H), 1.16 (t, J=8 Hz, 3H). NMR data of N,N'-(oxybis(4,1-phenylene)) bismaleimide (BMIPhO) are: $^1$H NMR (200 MHz, DMSO-d$_6$), δ 7.36 (d, J=6.8 Hz, 4H), 7.15 (d, J=6.8 Hz, 4H), 7.14 (s, 4H). NMR data of O-(methoxy-polyethylene glycol 550)-furfuryl acohol (FAmPEO) are: $^1$H NMR (200 MHz, CDCl$_3$), δ 7.34 (d, J=1.2 Hz, 1H), 6.30-6.23 (m, 2H), 4.55 (s, 2H), 3.92-3.40 (m, 44H), 3.18 (s, 3H). NMR data of O-(polyethylene glycol 200)-bisfurfuryl acohol (BFAPEO200) are: $^1$H NMR (200 MHz, CDCl$_3$), δ 7.37 (d, J=1.2 Hz, 2H), 6.33-6.27 (m, 4H), 4.58 (s, 4H), 3.91-3.21 (m, 10H).

For instance, the method for manufacturing an anode electrode plate of the present application comprises performing addition reactions of the unsaturated compounds having the maleimide functional groups and the carbon-containing substrates so that the diene functional groups or the dienophile functional groups of the unsaturated compounds form at least one chemical bond with the surfaces of the carbon-containing substrates. The addition reactions can be, for example, Diels-Alder reactions.

More specifically, in one embodiment, the graphitized MCMB and mesophase graphite (MPGA) as the anode active material (carbon-containing substrate) and BMI2300 are mixed and added into γ-butylactone (GBL) solvent (please refer to Table 1 in the following paragraph for the mixture ratio of the carbon-containing substrates (MPGA) to BMI2300), the concentrations of reactants in the reaction system are adjusted and the reaction temperature is controlled to be under 70° C. The reaction lasts for about four days. Then, after the reaction system is cooled down to the room temperature, the products are filtered by centrifuge. The products are repeatedly washed by using ultrasonic vibration with tetrahydrofuran (THF). After being dried in 50° C., the thermal gravimetric analysis (TGA) and scanning electronic microscopic (SEM) analysis are performed on the products. The weight ratio of the carbon-containing substrates to the unsaturated compounds is about 10:1~1:10.

The Table 1 listed below shows Raman spectrum analysis data and X-ray photoelectron spectrometer (XPS) analysis data of the products while the addition reactions of the carbon-containing substrates and the unsaturated compounds are performed under different reactant concentrations, different reaction temperatures and different reaction durations. As shown in Table 1, by analyzing the products obtained from the reactions of the carbon-containing substrates (MPGA) and BMI2300 under different reaction conditions, it reveals that the number of the BMI2300 on the carbon-containing substrates can be increased by increasing the concentrations of the reactants, the reaction temperature or the reaction duration.

TABLE 1

| Entry | MPGA | BMI2300 | GBL | T(° C.) | time | C(%) | N(%) | O(%) | $I_G/I_D$ |
|---|---|---|---|---|---|---|---|---|---|
| 1 | 10 g | 1.0 g | 50 mL | 70 | 96 h | 91.78 | 1.58 | 6.54 | 2 |
| 2 | 10 g | 5.0 g | 50 mL | 70 | 96 h | 89.97 | 2.55 | 7.48 | 1.88 |
| 3 | 10 g | 5.0 g | 50 mL | 130 | 96 h | 88.69 | 3.00 | 8.02 | 1.35 |
| 4 | 10 g | 5.0 g | 50 mL | 130 | 24 h | 6.54 | 7.48 | 8.20 | 1.78 |
| 5 | | | pristine MPGA | | | | | | 2 |

Moreover, in Raman spectrum, the feature peaks of the carbon-containing substrates are found around 1580 $cm^{-1}$ and 1340 $cm^{-1}$. The former is G-band which is generated from the carbon molecules vibrating along the planar direction of the graphite and can be regarded as the graphitization degree. The later is D-band which is generated from the structural defect or the edge of the carbon material. That is, the stronger the intensity of the D-band is, the more fragmented the structure of the graphite is. The larger IG/ID ratio obtained from the intensity of G-band is divided by the total intensity means the graphitization degree of the carbon-containing substrates is high and the amount of defects is small. The result of the addition reactions shows that the amount of carbon-carbon double bonds on the carbon-containing substrates is decreased. On the other words, the addition reactions lead to the decreasing of the graphitization degree of the carbon-containing substrates and the surfaces of the carbon-containing substrates are, indeed, modified by performing the addition reactions to form the chemical bonds between the surfaces of the carbon-containing substrates and the unsaturated compounds.

Further, the XPS result shows that the relative proportions of the nitrogen element, the oxygen element and the carbon element of the surfaces of the carbon-containing substrates can be controlled by adjusting the reaction temperature, the concentration of the reactants and the reaction duration so that the bonding degree between the diphenylmethane bismaleimide and the surfaces of the carbon-containing substrates can be indirectly controlled.

Figure 3A:
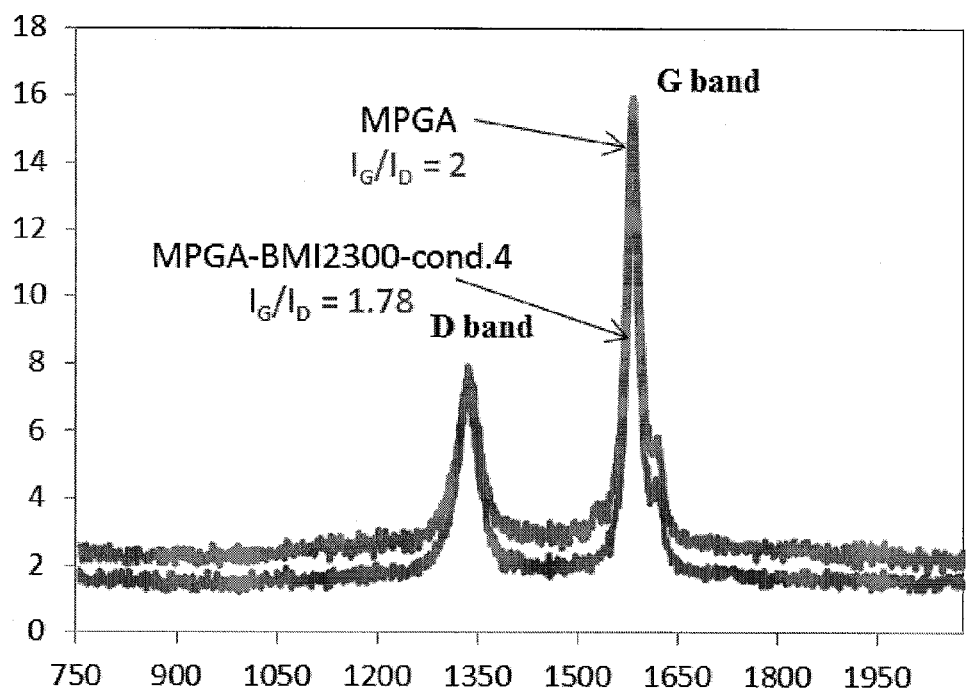
FIGS. 3A through 3D are Raman spectrums of the surfaces of the carbon-containing substrates modified by chemical bonding with four different unsaturated compounds.
Figure 3B:
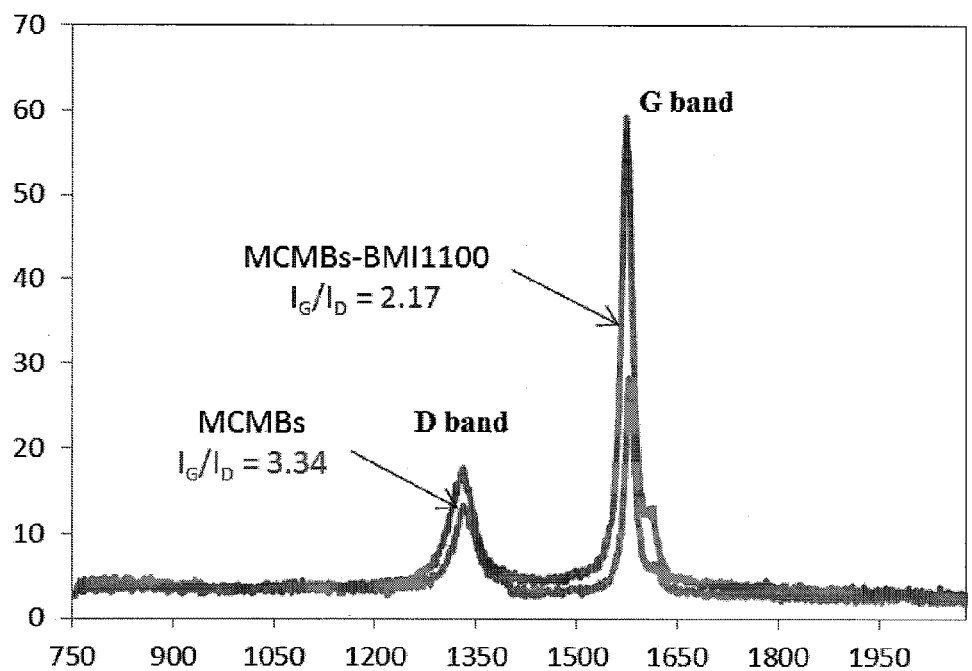
Figure 3C:
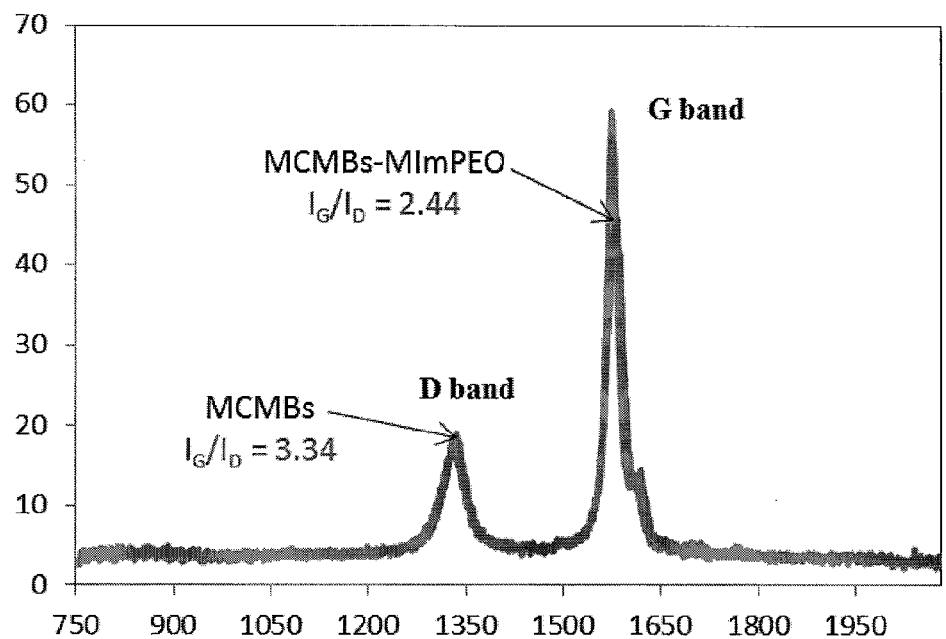
Figure 3D:
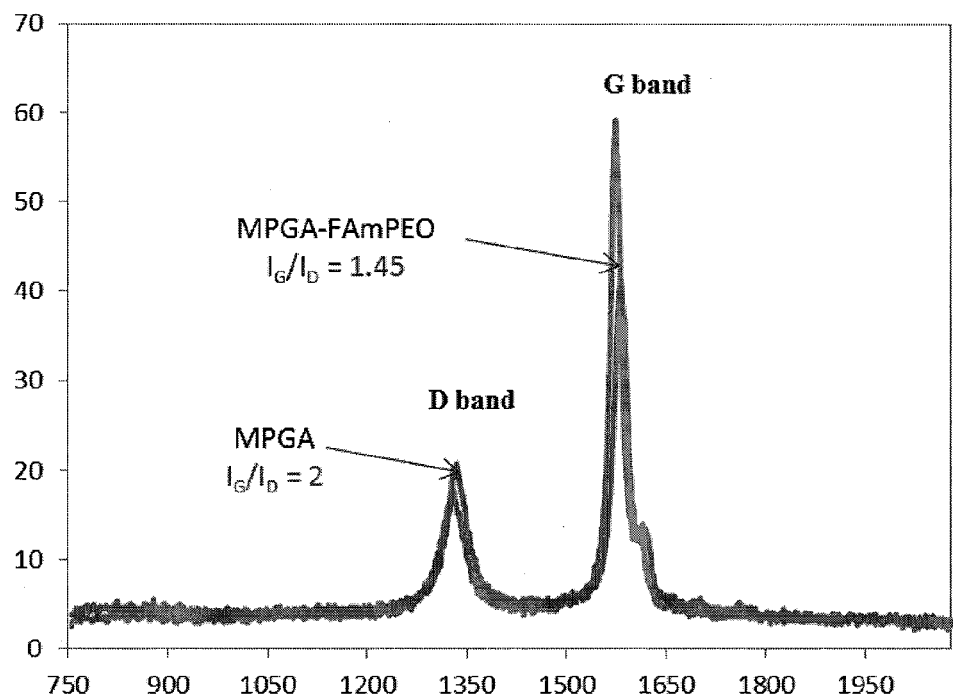

FIGS. 3A through 3D are Raman spectrums of the surfaces of the carbon-containing substrates modified by chemical bonding with four different unsaturated compounds. As shown in FIG. 3A, MPGA is used as the carbon-containing substrate and BMI2300 forms chemical bonds with the surfaces of the carbon-containing substrates. FIG. 3A shows 623.8 nm-wavelength He—Ne laser (2 mW) Raman spectrum of the carbon-containing substrates modified by BMI2300 and 623.8 nm-wavelength He—Ne laser (2 mW) Raman spectrum of the original carbon-containing substrates. Comparing to the original carbon-containing substrates, the graphitization degree of the carbon-containing substrates modified by BMI2300 is decreased (IG/ID ratio is decreased from 2 to 1.78), which means BMI2300, indeed, forms chemical bonds with the surfaces of the carbon-containing substrates. As shown in FIG. 3B, MCMB is used as the carbon-containing substrate and BMI1100 forms chemical bonds with the surfaces of the carbon-containing substrates. FIG. 3B shows 623.8 nm-wavelength He—Ne laser (2 mW) Raman spectrum of the carbon-containing substrates modified by BMI1100 and 623.8 nm-wavelength He—Ne laser (2 mW) Raman spectrum of the original carbon-containing substrates. Comparing to the original carbon-containing substrates, the graphitization degree of the carbon-containing substrates modified by BMI1100 is decreased (IG/ID ratio is decreased from 3.34 to 2.17), which means BMI1100, indeed, forms chemical bonds with the surfaces of the carbon-containing substrates. As shown in FIG. 3C, MCMB is used as the carbon-containing substrate and MImPEO forms chemical bonds with the surface of the carbon-containing substrates. FIG. 3C shows 623.8 nm-wavelength He—Ne laser (2 mW) Raman spectrum of the carbon-containing substrates modified by MImPEO and 623.8 nm-wavelength He—Ne laser (2 mW) Raman spectrum of the original carbon-containing substrates. Comparing to the original carbon-containing substrates, the graphitization degree of the carbon-containing substrates modified by MImPEO is decreased (IG/ID ratio is decreased from 3.34 to 2.44), which means MImPEO, indeed, forms chemical bonds with the surfaces of the carbon-containing substrates. As shown in FIG. 3D, MPGA is used as the carbon-containing substrate and FAmPEO forms chemical bonds with the surfaces of the carbon-containing substrates. FIG. 3D shows 623.8 nm-wavelength He—Ne laser (2 mW) Raman spectrum of the carbon-containing substrates modified by FAmPEO and 623.8 nm-wavelength He—Ne laser (2 mW) Raman spectrum of the original carbon-containing substrates. Comparing to the original carbon-containing substrates, the graphitization degree of the carbon-containing substrates modified by FAmPEO is decreased (IG/ID ratio is decreased from 2 to 1.45), which means FAmPEO, indeed, forms chemical bonds with the surfaces of the carbon-containing substrates.

Figure 4:
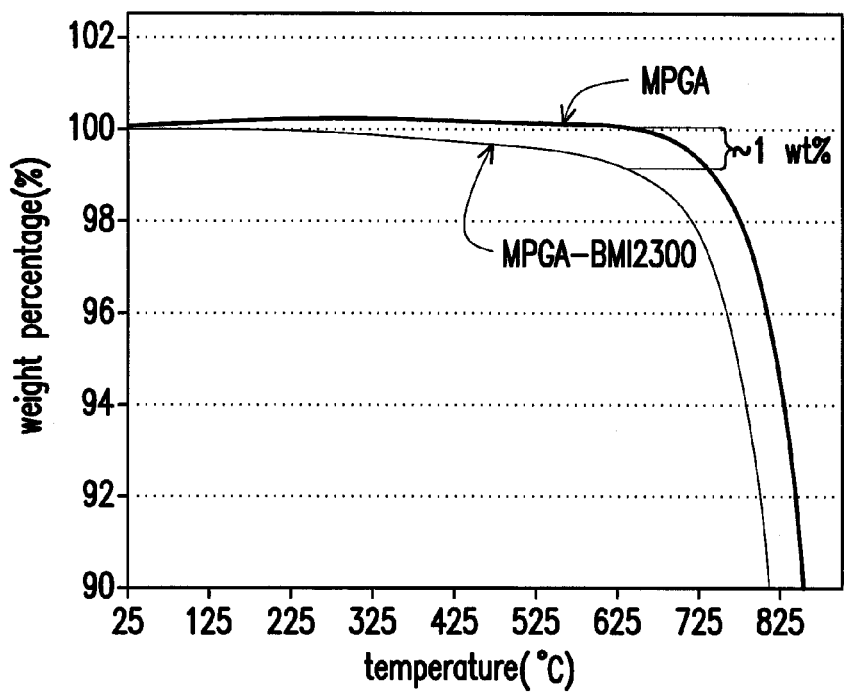
FIG. 4 is a plot diagram showing the thermal gravimetric analysis results of the surfaces of the carbon-containing substrates before and after the surfaces are modified by chemical bonding with the BMI2300 unsaturated compounds.

FIG. 4 is a plot diagram showing the thermal gravimetric analysis results of the surfaces of the carbon-containing substrates before and after the surface is modified by chemical bonding with the BMI2300 unsaturated compounds. As shown in FIG. 4, MPGA is used as the carbon-containing substrate and BMI2300 forms chemical bonds with the surfaces of the carbon-containing substrates to modify the surfaces of the carbon-containing substrates. The result of the thermal gravimetric analysis shows that, after the surfaces of the carbon-containing substrates is modified, the weight percentage of BMI2300 thereon to the carbon-containing substrates is about 1 wt %.

Figure 5:
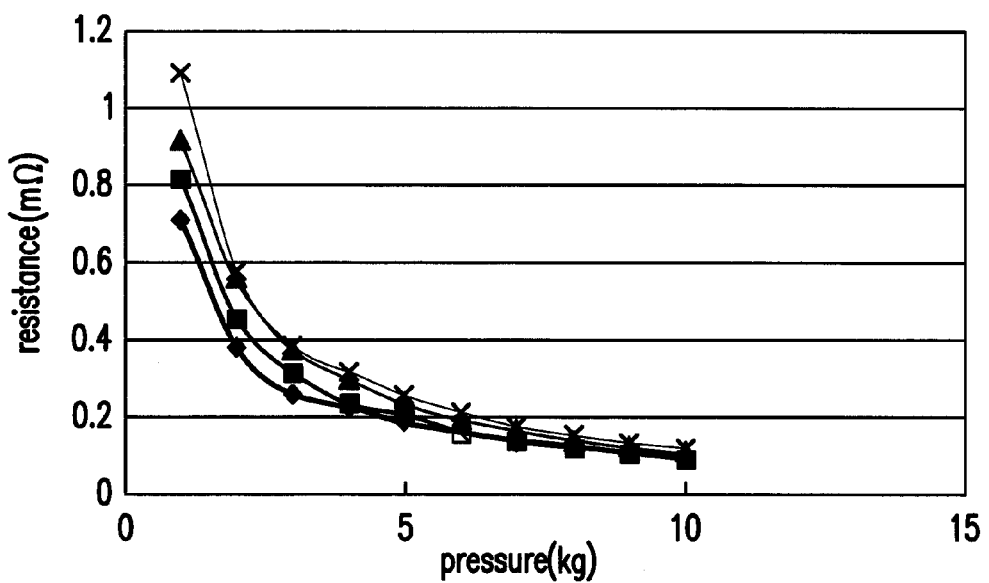
FIG. 5 is a plot diagram showing the variations of the conductivities of the powder bodies of the carbon-containing substrates before and after the surfaces of the powder bodies are modified by chemically bonding with the BMI2300 unsaturated compounds.

FIG. 5 is a plot diagram showing the variations of the conductivities of the powder bodies of the carbon-containing substrates before and after the surfaces of the powder bodies are modified by chemical bonding with the BMI2300 unsaturated compounds.

Figure 6A:
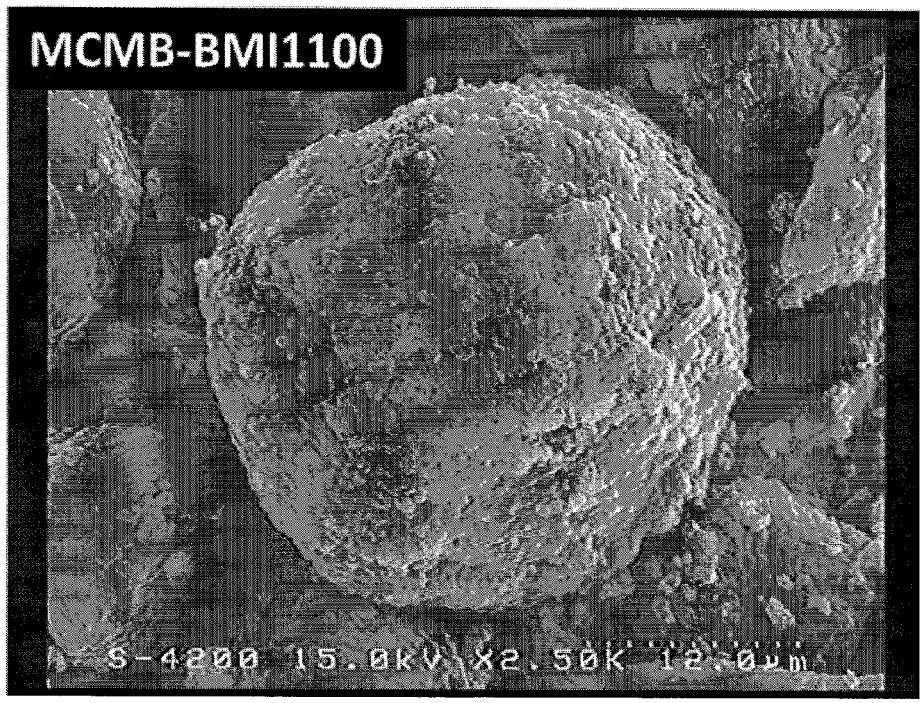
FIGS. 6A through 6C are Scanning Electron Microscopies respectively showing the surface contours of the carbon-containing substrates after the surfaces of the carbon-containing substrates are modified.
Figure 6B:
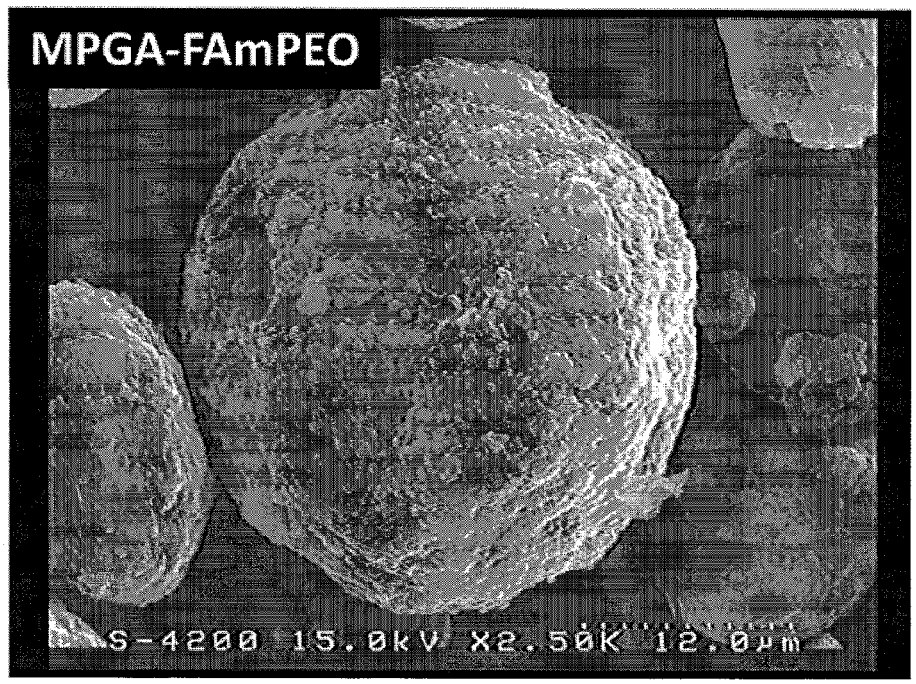
Figure 6C:
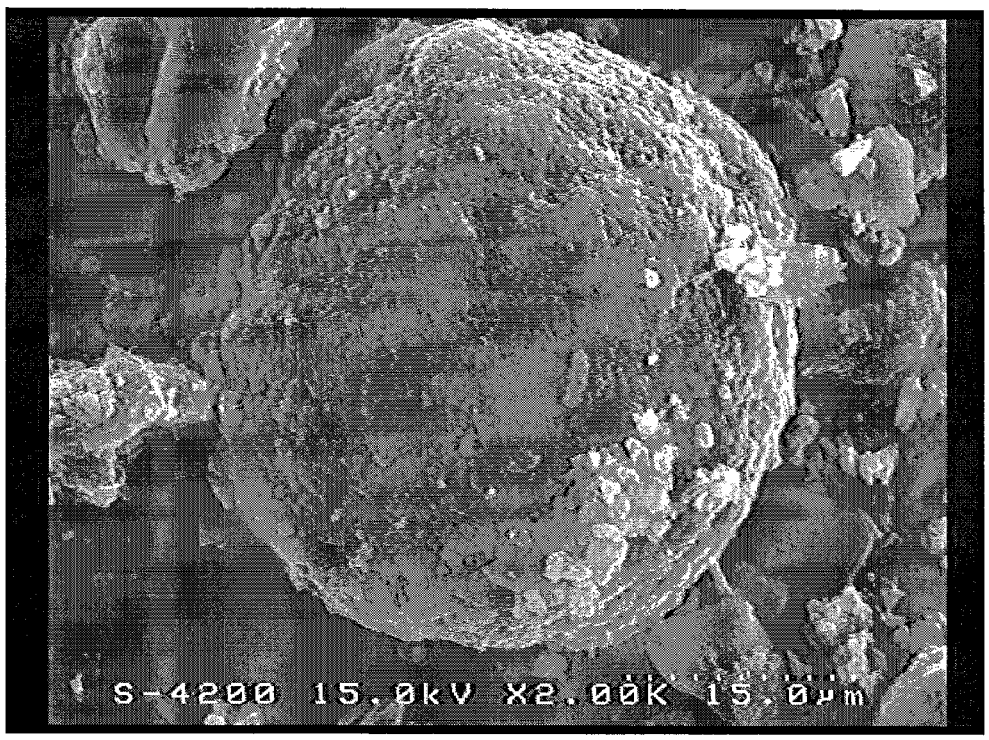

FIGS. 6A through 6C are Scanning Electron Microscopies respectively showing the surface contours of the carbon-containing substrates after the surfaces of the carbon-containing substrates are modified. FIG. 6A shows the scanning electron microscopy of the surface contour of the carbon-containing substrates after the surfaces of the carbon-containing substrates are modified by BMI1100 forming chemical bonds with the surfaces of the carbon-containing substrates while MCMB is used as the carbon-containing substrate. FIG. 6B shows the scanning electron microscopy of the surface contour of the carbon-containing substrates after the surfaces of the carbon-containing substrates are modified by FAmPEO forming chemical bonds with the surfaces of the carbon-containing substrates while MPGA is used as the carbon-containing substrate. FIG. 6C shows the scanning electron microscopy of the surface contour of the carbon-containing substrates after the surfaces of the carbon-containing substrates are modified by MimEO forming chemical bonds with the surfaces of the carbon-containing substrates while MCMB is used as the carbon-containing substrate.

Figure 7A:
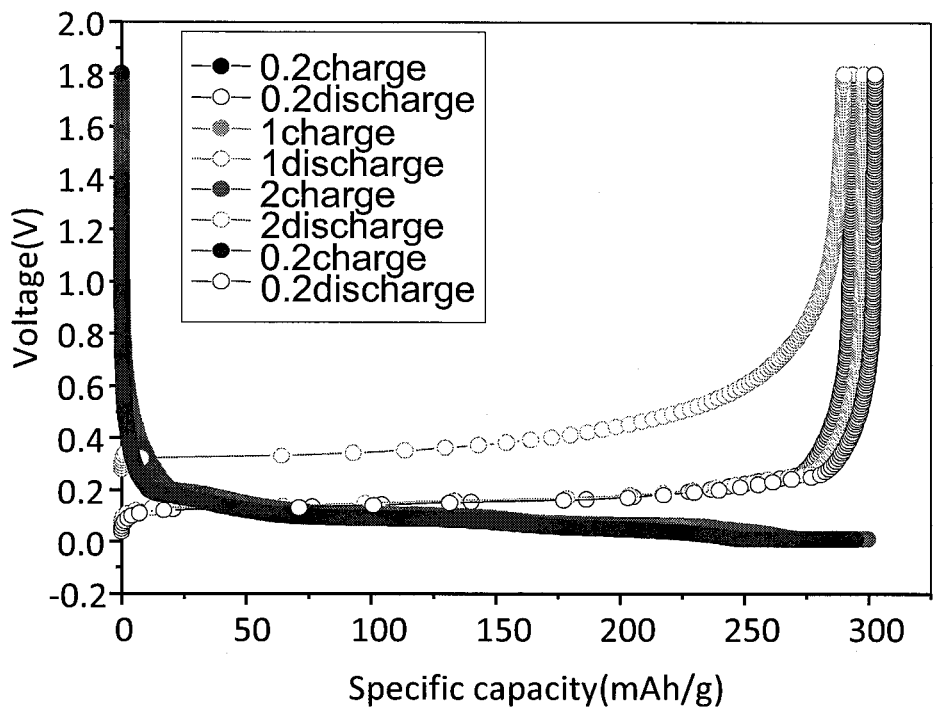
FIGS. 7A through 7C are diagrams respectively showing the charge rate plot diagram and the electrochemical efficiency table of the carbon-containing substrates before and after the surfaces of the carbon-containing substrates are modified by chemically bonding with the unsaturated compounds having monofuran functional groups and by chemically bonding with the unsaturated compounds having bisfuran functional groups.
Figure 7B:
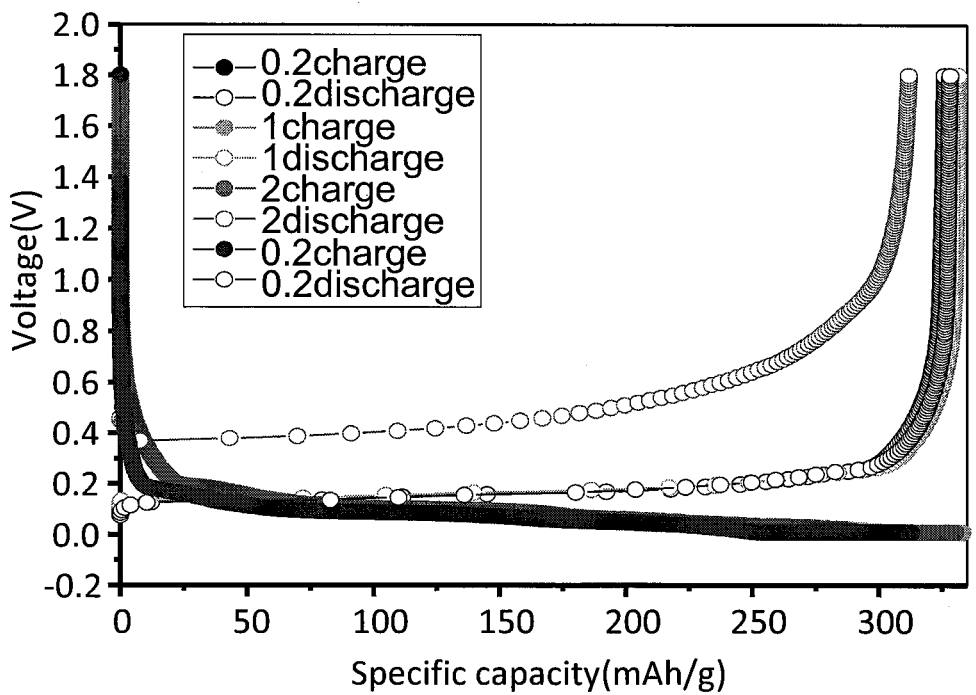
Figure 7C:
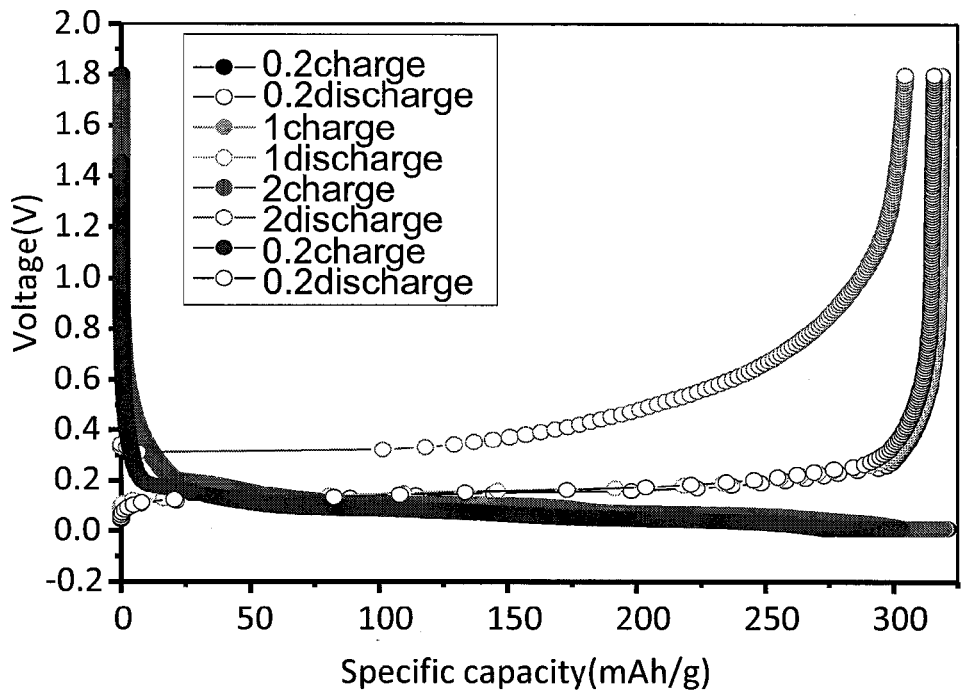

Table 2 shows the amount of the reactants and the analysis results of the products of the addition reactions of the carbon-containing substrates and five different unsaturated compounds while MCMB is used as the carbon-containing substrate.

of the carbon-containing substrates before and after the surfaces of the carbon-containing substrates are modified by chemical bonding with the unsaturated compounds. FIGS. 7A through 7C are diagrams respectively showing the charge rate plot diagram and the electrochemical efficiency table of the carbon-containing substrates before and after the surfaces of the carbon-containing substrates are modified by chemically bonding with the unsaturated compounds having monofuran functional groups and by chemically bonding with the unsaturated compounds having bisfuran functional groups. As shown in FIGS. 7A through 7C, while MPGA is used as the carbon-containing substrate, the charge-discharge capacity (XC/0.2C) of the carbon-containing substrates after being modified by the unsaturated compounds is larger than 90%. Apparently, the solid-liquid interface can be improved by the unsaturated compounds modifying the surfaces of the carbon-containing substrates, and the wetness between the modified carbon-containing substrates and the electrolyte is enhanced so that it is beneficial to the capacitance.

Figure 8:
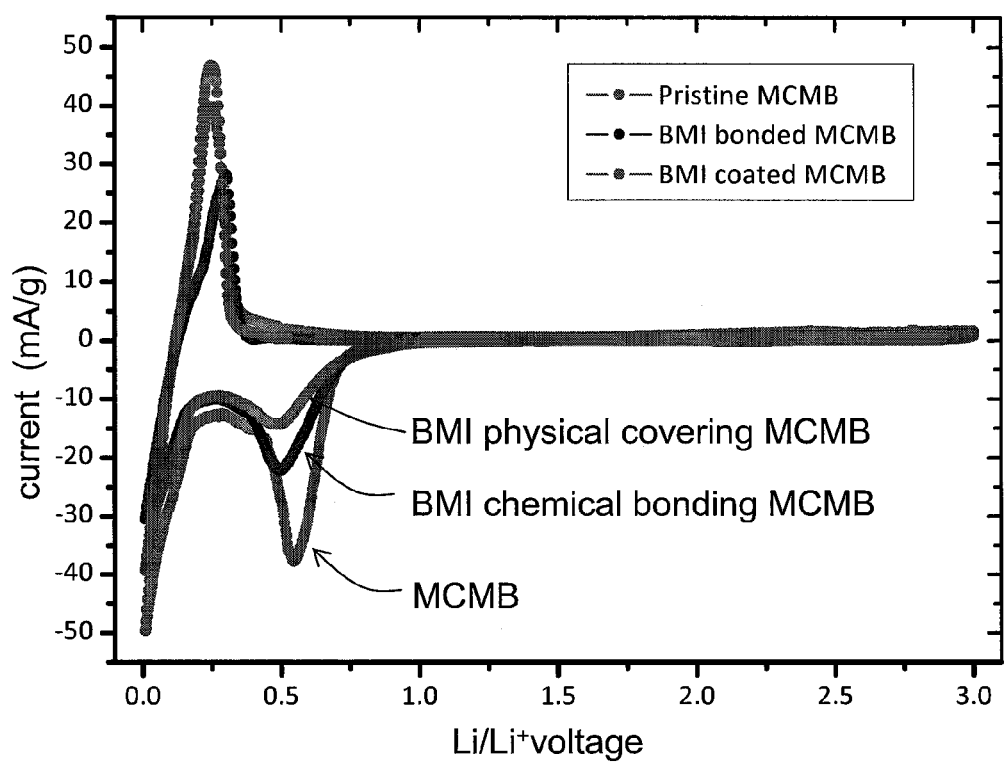
FIG. 8 is a plot diagram obtained by applying the cyclic voltammetry onto the anode electrode plate and showing the current-voltage variations of the carbon-containing substrates before and after the surfaces of the carbon-containing substrates is modified by chemically bonding with the unsaturated compounds having maleimide functional groups and by being physical covered with the surface modifier.

FIG. 8 is a plot diagram obtained by applying the cyclic voltammetry onto the anode electrode plate and showing the current-voltage variations of the carbon-containing substrates before and after the surfaces of the carbon-containing substrates are modified by chemically bonding with the unsaturated compounds having maleimide functional groups and by being physical covered with the surface modifier. As shown in FIG. 8, while MCMB is used as carbon-containing substrate, the cyclic voltammery (CV) test shows that the reduction potential drops at 0.53 voltage. Further, on the anode electrode plate, the carbon-containing substrates modified by unsaturated compounds having maleimide functional groups and forming chemical bonds with the surfaces of the carbon-containing substrates effectively suppresses the high polar solvent (which is attracted by the lithium ions to occur solvation) inserting the interlayer structures of the carbon-containing substrates with the lithium ions.

TABLE 2

| unsaturated compounds | (g) | MCMB | GBL | T(° C.) | time | C(%) | N(%) | O(%) | $I_G/I_D$ |
|---|---|---|---|---|---|---|---|---|---|
| BMI1100 | 4.50 | 10 g | 50 mL | 70 | 96 h | 95.2 | 1.08 | 3.68 | 2.17 |
| MImEO | 2.70 | 10 g | 50 mL | 70 | 96 h | 97.05 | 0.03 | 2.92 | 2.00 |
| MImPEO | 7.85 | 10 g | 50 mL | 70 | 96 h | 97.68 | 0 | 2.32 | 2.44 |
| BMID400 | 8.90 | 12 g | 50 mL | 70 | 96 h | 97.67 | 0.01 | 2.32 | 2.77 |
| BMIPhO | 4.5 | 10 g | 50 mL | 70 | 96 h | 97.64 | 0.08 | 2.28 | 2.38 |
| Pristine MCMBs | | | | | | | | | 3.34 |

Table 3 shows the result of the addition reactions of the unsaturated compounds FAmPEO having diene functional groups and the surfaces carbon-containing substrates and the result of the addition reactions of the unsaturated compounds BFAPEO200 having diene functional groups and the surfaces carbon-containing substrates.

The anode material obtained from the aforementioned embodiment is disposed on the current collector to form an anode electrode plate. The anode material, the conducting agent and the binder are mixed together according to a mixing ratio. For instance, the anode material of 90 wt. %, the conducting agent of 5 wt. % and the binder of 5 wt. % are mixed

TABLE 3

| unsaturated compounds having diene functional groups | (g) | MPGA | GBL | T(° C.) | time | C(%) | N(%) | O(%) | $I_G/I_D$ |
|---|---|---|---|---|---|---|---|---|---|
| FAmPEO | 6.3 | 10 g | 100 mL | 70 | 96 h | 94.2 | 0 | 6.54 | 1.45 |
| BFAPEO200 | 7.0 | 10 g | 100 mL | 70 | 96 h | 95.95 | 0 | 3.95 | 1.92 |
| Pristine MPGA | | | | | | | | | 2.00 |

Several analysis exemplars are given in the followings to describe electrochemical property variations of the surfaces together and the mixture is disposed on the current collector. In one embodiment, an anode material having a diameter of about 1~30 μm and a weight percentage of about 90 wt. % and fluorine resin with a weight percentage of about 3~10 wt. % as a binder are dissolved in N-methyl-2-pyrrolidinone (NMP). After being mixed well, the solution is spread onto a copper foil roll with a length of about 300 m, a width of about 35 cm and a thickness of about 10 μm to form an anode roll. After being compressed, the compressed anode roll is dried in a vacuum of 110° C. for four hours to accomplish the manufacturing of the anode electrode plate.

Altogether, in the present application, addition reactions are performed between the functional groups of the unsaturated chemical compounds and the surfaces of the carbon-containing substrates to form chemical bonds such as covalent bonds and mechanism of the addition reaction is reversible. When a portion of the crosslinking structures of the polymer of the unsaturated compounds which form chemical bonds with the surfaces of the carbon-containing substrates is damaged by the external factors (such as heat or stress), the damaged crosslinking structures can recover from applying energy (such as heating) onto the polymer to perform the addition reactions again due to the reversibility of the addition reaction. Thus, on the surfaces of the carbon-containing substrates, the protective layers which are made of the unsaturated chemical compounds having chemical bonds with the surfaces of the carbon-containing substrates possess self-hilling ability. Moreover, the protective layers which are formed from the unsaturated chemical compounds on the carbon-containing substrates can effectively suppress the high polar solvent (which is attracted by the lithium ions to occur solvation) inserting the interlayer structures of the carbon-containing substrates with the lithium ions. Therefore, the structure stability of the anode material in the electrochemical reactions can be retained, the long term charge-discharge cycle time of the battery can be prolonged and the capacitance irreversibility due to structural damage can be decreased. Moreover, since the surface potential of the modified carbon-containing substrates is increased due to the bonding between the unsaturated compounds and the surfaces of the carbon-containing substrates, the anode electrode plate can be effectively soaked through in the high polar electrolyte. Hence, the resistance of the solid-liquid interface between the carbon-containing substrates and the electrolyte can be decreased. That is, the protective layers formed on the carbon-containing substrates can improve the electrochemical activity of the surfaces of the carbon-containing substrates so as to improve the compatibility between the surfaces of the carbon-containing substrates and the electrolyte and, meanwhile, to preserve the unity of the carbon-containing substrates.

It will be apparent to those skilled in the art that various modifications and variations can be made to the structure of the present application without departing from the scope or spirit of the application. In view of the foregoing descriptions, it is intended that the present application covers modifications and variations of this application if they fall within the scope of the following claims and their equivalents.

What is claimed is:
1. An anode material for a surface of an electrode plate, the anode material being consisting of:
  carbon-containing substrates; and
  unsaturated compounds, wherein at least a chemical bond is formed between the unsaturated compounds and the carbon-containing substrates, and the unsaturated compounds are represented by a chemical formula (I) shown as following:

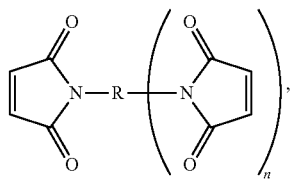

wherein R comprises at least a unit of ethylene oxide segment, propylene oxide segment, siloxane segment, aliphatic segment, aromatic segment, fluorocarbon segment or the combination thereof, and n is 1-3.

2. The anode material of claim 1, wherein a weight percentage of the unsaturated compounds to the carbon-containing substrates is smaller than 15 wt %.

3. The anode material of claim 1, wherein the thickness of the unsaturated compounds is about 5~500 nm.

4. The anode material of claim 1, wherein a graphitization degree of the carbon-containing substrates is about 50%~90%.

5. The anode material of claim 1, wherein the carbon-containing substrates comprise graphite, graphene, hard carbon, soft carbon, single-wall carbon nano-tubes (SWCNT), multi-wall carbon nano-tubes (MWCNT), carbon fiber, carbon alloy, carbon metal oxide, silicon carbon composite (Si/C composite), mesophase carbon micro beads (MCMB), mesophase graphite, mesoporous graphite or the combination thereof.

6. An anode electrode plate, comprising:
  a current collector; and
  an anode material layer disposed on the current collector, wherein the anode material layer is consisted of carbon-containing substrates and unsaturated compounds, and at least a chemical bond is formed between the unsaturated compounds and the carbon-containing substrates, and the unsaturated compounds are represented by a chemical formula (I) shown as following:

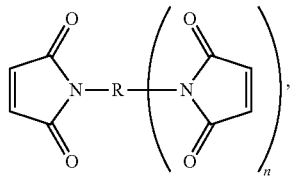

wherein R comprises at least a unit of ethylene oxide segment, propylene oxide segment, siloxane segment, aliphatic segment, aromatic segment, fluorocarbon segment or the combination thereof, and n is 1-3.

7. The anode electrode plate of claim 6, wherein a weight percentage of the unsaturated compounds to the carbon-containing substrates is smaller than 15 wt %.

8. The anode electrode plate of claim 6, wherein the thickness of the unsaturated compounds is about 5~500 nm.

9. The anode electrode plate of claim 6, wherein a graphitization degree of the carbon-containing substrates is about 50%~90%.

10. The anode electrode plate of claim 6, wherein the carbon-containing substrates comprises graphite, graphene, hard carbon, soft carbon, single-wall carbon nano-tubes (SWCNT), multi-wall carbon nano-tubes (MWCNT), carbon fiber, carbon alloy, carbon metal oxide, silicon carbon composite (Si/C composite), mesophase carbon micro beads (MCMB), mesophase graphite, mesoporous graphite or the combination thereof.

11. The anode electrode plate of claim 6, wherein the anode material layer further comprises a conducting agent and a binder.

* * * * *